United States Patent
Emekci

(10) Patent No.: US 8,931,129 B2
(45) Date of Patent: Jan. 13, 2015

(54) TREATMENT DEVICE

(75) Inventor: Bülent Emekci, Mörfelden-Walldorf (DE)

(73) Assignee: Emag AG, Mörfelden-Walldorf (DE)

( * ) Notice: Subject to any disclaimer, the term of this patent is extended or adjusted under 35 U.S.C. 154(b) by 21 days.

(21) Appl. No.: 13/643,363

(22) PCT Filed: Oct. 28, 2011

(86) PCT No.: PCT/DE2011/001918
§ 371 (c)(1),
(2), (4) Date: Jan. 2, 2013

(87) PCT Pub. No.: WO2012/062277
PCT Pub. Date: May 18, 2012

(65) Prior Publication Data
US 2013/0115571 A1  May 9, 2013

(30) Foreign Application Priority Data

Nov. 9, 2010 (DE) .................... 20 2010 015 189 U

(51) Int. Cl.
*A61C 17/20* (2006.01)
*A61C 17/22* (2006.01)
*A46B 13/02* (2006.01)
*A61C 17/34* (2006.01)

(52) U.S. Cl.
CPC ............ *A61C 17/3436* (2013.01); *A61C 17/20* (2013.01); *A61C 17/3481* (2013.01); *A61C 17/221* (2013.01); *A61C 17/224* (2013.01); *A61C 17/225* (2013.01); *A61C 17/222* (2013.01)
USPC ............................. 15/22.1; 433/118; 433/119

(58) Field of Classification Search
USPC ..................................... 15/22.1; 433/118, 119
See application file for complete search history.

(56) References Cited

U.S. PATENT DOCUMENTS

| | | | |
|---|---|---|---|
| 5,546,624 | A | 8/1996 | Bock |
| 7,269,873 | B2 * | 9/2007 | Brewer et al. .................. 15/22.1 |
| 2010/0237720 | A1 | 9/2010 | Taylor |

FOREIGN PATENT DOCUMENTS

| | | | |
|---|---|---|---|
| DE | 1632390 | | 11/1970 |
| DE | 69325373 | | 10/1999 |
| DE | 20120955 | | 5/2002 |
| DE | 20218605 | | 6/2003 |
| DE | 10243678 | * | 4/2004 |
| DE | 102005007617 | | 9/2006 |
| DE | 202009003586 | | 6/2009 |
| GB | 2250428 | | 6/1992 |
| JP | H07-509151 | | 10/1995 |
| JP | 10-066704 | | 3/1998 |
| JP | 2002-513297 | | 5/2002 |
| JP | 2003-245288 | * | 9/2003 |
| JP | 2004-41684 | * | 2/2004 |
| JP | 2004-57534 | * | 2/2004 |
| JP | 2004-89353 | * | 3/2004 |

(Continued)

*Primary Examiner* — Mark Spisich
(74) *Attorney, Agent, or Firm* — Welsh, Flaxman & Gitler LLC

(57) ABSTRACT

Treatment device for treatment of the oral cavity and pharynx and/or the teeth, having a treatment head that can be removably fastened to a handpiece, and which has a head piece having a plurality of bristles and which has an electromechanical transducer in the head piece for producing a mechanical oscillation or waves to be transferred to a treatment area.

12 Claims, 1 Drawing Sheet

(56) References Cited

FOREIGN PATENT DOCUMENTS

| JP | 2006-149474 | | 6/2006 |
|----|-------------|---|--------|
| JP | 2007-61209 | * | 3/2007 |
| WO | WO2006/119376 | | 11/2006 |
| WO | 2009/006760 | * | 1/2009 |
| WO | WO2009/116481 | | 9/2009 |
| WO | WO2009108262 | | 9/2009 |
| WO | WO2010/076703 | | 7/2010 |

* cited by examiner

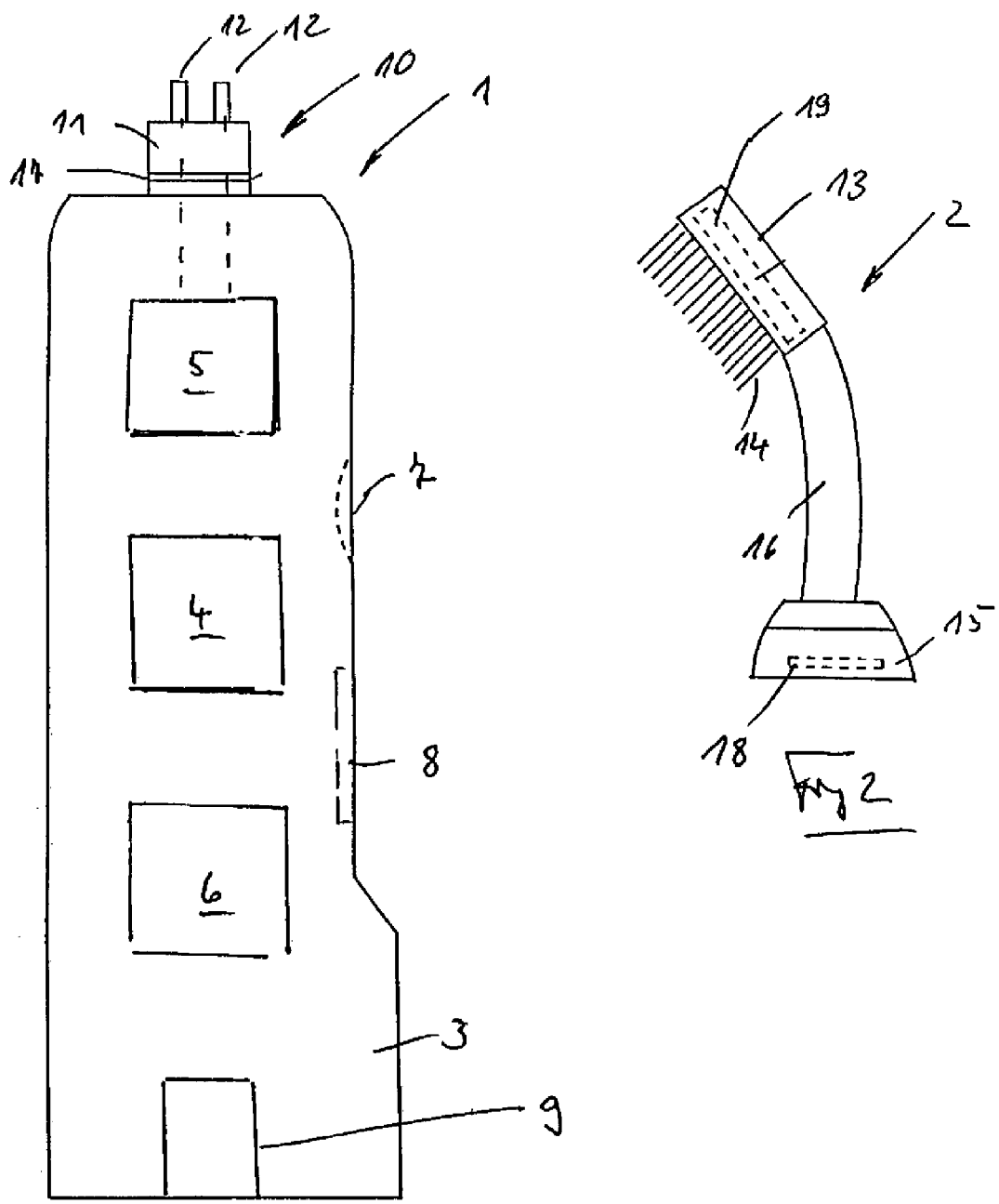

TREATMENT DEVICE

BACKGROUND OF THE INVENTION

The invention relates to a treatment device. The treatment device is used for treatment of the oral cavity, the pharynx and/or the teeth.

Treatment devices, in particular, for oral and dental care, are known in the art and are also referred to as ultrasonic devices or ultrasonic dental treatment devices.

It is an object of the present invention to provide a treatment device for optimal cleaning and for prophylactic and/or therapeutic effects in the oral region, therefore achieving oral and/or dental hygiene of an unprecedented quality.

SUMMARY OF THE INVENTION

According to one fundamental aspect of the invention, bristles are provided on the head piece of the treatment head for the mechanical oscillations which are produced when the bristles are coupled to at least one electromechanical transducer placed in the head piece. The electromechanical transducer produces the mechanical oscillations, so that the bristles oscillate and function as waveguides and thereby transfer the mechanical oscillation energy with their free end as directly and undamped as possible to the respective treatment area. The one or more electromechanical transducers are designed so that at least the main direction of the mechanical oscillations, produced by the transducer, has a parallel or essentially parallel orientation to the longitudinal extension of the bristles, i.e. the mechanical oscillations or the waves of the mechanical oscillations produced by the one or more electromechanical transducers are transferred directly into the bristles.

The frequency of the mechanical oscillations is at least 60 KHz; preferably, the frequency of the mechanical oscillations is between 60 KHz and 2 MHz. The electrical power for operation of the at least one electromechanical transducer is preferably less than 50 W, so that the oscillation energy transferred by the treatment head to the bristles is clearly below a value that could result in damage to the tissue in the respective treatment area.

The electronic circuit accommodated in the handpiece for generating the electrical voltage for driving the at least one electromechanical transducer is designed, for example, so that when a load or its mechanical power exceeds a predefined threshold at the head piece or at the bristles, the power driving the at least one electromechanical transducer is automatically reduced, for example, by monitoring and/or limiting the current supplied to the at least one electromechanical transducer.

One effect of the embodiment, according to the invention, is that when the treatment device is used in suitable media (e.g. liquids) or when it is used during treatment, small cavitations are formed by the oscillation energy transferred by the bristles to the treatment area, especially in the area of the free ends of the bristles. As a result of implosion, these cavitations loosen impurities and films from teeth and kill germs and bacteria in the treatment area. The cavitations thus created have a diameter that is many times smaller than the diameter of bacteria, so that upon implosion of the microcavitations, the nucleus of the bacteria, and therefore the bacteria themselves, are destroyed and killed. The waves, transferred by the electromechanical transducer, are also suitable for penetrating into the tissue and killing bacteria, bacteria nests or germs with a prophylactic and/or therapeutic effect. Simultaneously, this process activates increased circulation of blood through the tissue and releases the body's natural energies, thus reinforcing the body's natural immune system due to the oscillation energy. Consequently, the treatment with the treatment device not only has a prophylactic effect, but also exhibits a therapeutic effect, since mechanical oscillation energy in the ultrasonic range penetrates up to a depth of 12 mm into the tissue or the gums. This therapeutic effect is especially pronounced in the case of acute inflammations, e.g. of the gums or roots of the teeth.

Further embodiments, advantages and possible applications of the invention are disclosed by the following description of exemplary embodiments and the drawings. All characteristics described and/or pictorially represented, alone or in any combination, are subject matter of the invention.

BRIEF DESCRIPTION OF THE DRAWINGS

The invention is described in more detail below based on an exemplary embodiment with reference to the drawings, in which:

FIG. 1 is a schematic representation in side view of the handpiece of a treatment device according to the invention; and FIG. 2 is a schematic representation in side view of the treatment head for use with the handpiece in FIG. 1.

DETAILED DESCRIPTION OF THE INVENTION

The handpiece generally designated 1 in the drawings is part of a treatment device for optimal oral and/or dental hygiene. The treatment device, in addition to the handpiece 1, comprises at least one treatment head 2, which is removably fastened to the handpiece 1. The handpiece 1 in the depicted embodiment has an elongated, for example, cylindrical or approximately cylindrical, housing 3. The handpiece 1 or the housing 3 accommodates different functional elements of the treatment device, including at least one rechargeable battery 4, one electronic circuit 5, and vibrator 6. The electronic circuit 5 generates an output voltage in the ultrasonic or high-frequency range, e.g. with a frequency above 60 KHz, and preferably, with a frequency in the range between 60 KHz and 2 MHz. The vibrator 6, for example, is composed of a miniature motor having an imbalance. The vibrator 6 is activated when the handpiece 1 is switched on and serves only to indicate the activated state of the hand-held device, audibly and, in particular, also haptically.

Provided on the outside of the housing 3 are further functional elements. The functional elements include actuating elements 7 and display elements or displays 8. The actuating elements are, e.g., buttons, in particular, for switching the handpiece 1 on and off and/or for changing or setting the intensity of the treatment. The display elements or displays are provided in particular for displaying the respective operating state and/or errors, etc. of the treatment device. On the bottom side of the handpiece 1, there is a connection 9 for coupling the handpiece 1 to a charging device (not depicted). On the top side of the housing 3 a multi-coupler 10 is provided for mechanical and electrical coupling of the treatment head 2.

The multi-coupler 10 comprises a peg-like coupler section 11 protruding over the top side of the housing 3. The peg-like coupler section 11 has a non-circular cross section and forms the mechanical part of the multi-coupler 10. The multi-coupler 10 also includes at least two plug-like electrical connection elements 12 that form the electrical part of the multi-coupler 10. The at least two plug-like electrical connection elements 12 are connected with one control output of the electronic circuit 5. The housing 3 is manufactured, for example, from plastic.

The treatment head 2 consists essentially of a head piece 13 with a plurality of bristles 14 protruding on one side of the head piece, one mechanical and electrical coupler element 15 and one rod-shaped section 16 connecting the head piece 13 with the coupler element 15. In the depicted embodiment, the head piece 13, the coupler element 15 and the rod-shaped intermediate element 16 are manufactured as one piece from a suitable material, for example, from plastic. The coupler element 15 has a hood-like design and is open on the side facing away from the head piece 13, so that it can be pushed onto the coupler section 11 and fastened there by locking into place. Due to the non-circular cross section of the coupler section 11 and the accordingly adapted inner cross section of the coupler element 15, the treatment head 2, after being fastened to the handpiece 1, is held on the latter in a non-rotatable manner. More particularly, the fastening of the treatment head 2 to the handpiece 1 is facilitated by the provision of a counter-catch 18 on the treatment head 2 and catch 17 on the base of the peg-like coupler section 11 of the handpiece 1. The catch 17 and the counter-catch 18 are shaped and dimensioned for selective engagement in a manner fastening the treatment head 2 to the handpiece 1. Inside the coupler element 15, socket-like electrical connections, corresponding to the electrical connections 12, are provided and are connected by electrical wires accommodated in the intermediate element 16 with at least one electromechanical transducer accommodated in the head piece 13. As a result, after fastening and locking the coupler element 15 to the multi-coupler 10 of the handpiece 1, the at least one electromechanical transducer 19 is connected with the output of the electronic circuit. The at least one electromechanical transducer 19 consists, for example, of at least one piezo element. When the handpiece 1 is activated, the at least electromechanical transducer 19 is controlled by the output voltage of the electronic circuit 5, and produces a mechanical oscillation with a frequency greater than 60 KHz, preferably a frequency between 60 KHz and 2 MHz. In accordance with a preferred embodiment, the direction of propagation of the mechanical oscillations is perpendicular to the longitudinal extension of the transducer 19, i.e. in an axis direction that is the same, or essentially the same, as the axis direction of the longitudinal extension of the bristles 14. Each bristle 14 is connected on one end directly with the transducer 19, so that the mechanical oscillation produced by the transducer 19 is transferred directly and undamped to the respective bristle 14 or the end of the bristle 14 held in the head piece 13. Each bristle therefore directly forms one element for transfer of the mechanical oscillation on the other, free bristle end.

The electronic circuit 5 is designed so that the power output at the at least one transducer 19 is less than 50 W, preferably a maximum of 0.2 W. This ensures that the mechanical oscillation power transferred via the bristles 14 is below a value that could result in damage to the tissue during the treatment. Preferably, the electronic circuit 5 is designed so that in case of a high load on the bristles 14 and therefore on the transducer 19, the electrical power output from the electronic circuit 5 is automatically reduced. This automatic reduction in the electrical power output from the electronic circuit 5 is achieved, for example, by monitoring and/or controlling the electric current supplied to the at least one transducer 19.

To enable optimal treatment of the oral cavity and pharynx, and in particular optimal treatment of the teeth, the intermediate element 16 is curved, so that the bristles 14 are provided on the concave side of this curve.

As discussed above, the treatment device essentially consists of the handpiece 1 and the treatment head 2 and is ideally suitable for oral and dental hygiene. The direct coupling of the bristles 14 with the electromechanical transducer 19 achieves the production of oscillations producing microscopically small cavitations when the treatment device is used for treatment in suitable media, for example, in liquid media used during the treatment. These microscopically small cavitations destroy impurities through implosions, e.g. by loosening them from teeth and killing germs, e.g. bacteria. Further, the mechanical oscillations or waves are also suitable for penetrating into the tissue and killing any bacteria or bacteria nests there. This action results in a prophylactic and/or therapeutic effect achieved through the use of the present treatment device. By killing germs or bacteria and simultaneously activating increased circulation of blood through the tissue, releasing the body's natural energies and therefore reinforcing the body's natural immune system by means of the mechanical oscillations, the treatment device also has a preventive effect. In the case of acute inflammations, e.g. of the gums or roots of the teeth, these actions of the treatment device also achieve a therapeutic effect, especially since the mechanical oscillations, in particular in the ultrasonic range, penetrate up to a depth of 12 mm into the tissue or gums.

A special characteristic of the treatment device according to the invention is that the bristles 14 in the treatment head 2 are fastened deeply and with a direct connection to the electromechanical transducer 19 or ultrasonic generator on the treatment head 2.

Another special characteristic of the treatment device is that during operation the electronic circuit 5 monitors the functioning of the electromechanical transducer 19 in the head piece or treatment head 2 and that proper, or improper functioning, is indicated by a corresponding display on the housing 3 or on the display device 8.

Further, the electronic circuit 5 is equipped with a warning and monitoring function for the rechargeable battery 4. In particular, when the battery 4 is sufficiently charged, this status is indicated by a corresponding display, for example in green, and when the battery is insufficiently charged, this status is indicated by a flashing display, for example in red, on the display device 8.

The invention was described above based on an exemplary embodiment. It goes without saying that modifications and variations are possible, without abandoning the underlying inventive idea on which the invention is based.

REFERENCE LIST 1 handpiece
2 treatment head
3 housing
4 rechargeable battery
5 electronic circuit
6 vibrator
7 confirmation device
8 display device
9 connection
10 electromechanical multi-coupler
11 mechanical coupler section
12 electrical connections
13 head piece
14 bristles
15 coupler element
16 intermediate element
17 catch
18 counter-catch 19 electromechanical transducer

The invention claimed is:

1. A treatment device for teeth comprising:
a treatment head that is removably fastened to a handpiece, the treatment head includes a head piece comprising bristles and an electromechanical transducer in the head piece for producing mechanical oscillations or waves to be transferred to a treatment area, wherein all of the bristles of the head piece are directly connected on one end to the electromechanical transducer for transfer of the mechanical oscillations or waves in an axis direction parallel to a longitudinal extension of the bristles so that the mechanical oscillations or waves produced by the electromechanical transducer are transferred directly and undamped to the bristles, wherein all of the bristles of the head piece are directly connected on one end with the electromechanical transducer so that the mechanical oscillations are transferred directly and undamped to each bristle and each bristle forms one element for transfer of the mechanical oscillations to a free end of each bristle and wherein the handpiece comprises a vibrator comprised of a miniature motor, the vibrator is activated when the handpiece is switched on and the vibrator serves to mechanically or haptically indicate that the treatment device is activated.

2. The treatment device according to claim 1, wherein the miniature motor serves to audibly-indicate that the treatment device is activated.

3. The treatment device according to claim 1, wherein the electromechanical transducer transfers mechanical oscillations with a frequency between 60 KHz and 2 MHz.

4. The treatment device according claim 1, further comprising an electronic circuit in the handpiece for controlling the electromechanical transducer, the electronic circuit transfers an electric power output of less than 50 W to the electromechanical transducer.

5. The treatment device according to claim 4, wherein the electric power output of the electronic circuit is 0.2 W.

6. The treatment device according to claim 1, wherein the treatment head is removably locked onto the handpiece.

7. The treatment device according to claim 6, wherein the handpiece includes a housing having a coupler with a coupler section for fastening of the treatment head to the handpiece.

8. The treatment device according to claim 7, wherein a peg-like coupler section is formed as one part of the housing or is one piece and attached to the housing.

9. The treatment device according to claim 7, wherein the housing of the treatment device is hermetically sealed by ultra welding housing parts of the housing.

10. The treatment device according to claim 1, further comprising an electronic circuit in a housing of the treatment device with a monitoring and warning function for monitoring a voltage of a rechargeable battery accommodated in the housing, and further comprising on an outside of the housing at least one optical display that is controlled by a monitoring and warning function so that the at least one optical display is steadily illuminated when the rechargeable battery is sufficiently charged and flashes when a charge of the rechargeable battery is insufficient.

11. The treatment device according to claim 1, further comprising an electronic circuit accommodated in a housing with a control function for monitoring a correct functioning of the electromechanical transducer in the treatment head and controls a display on the housing that indicates a proper or improper functioning of the electromechanical transducer.

12. The treatment device according to claim 1, wherein the electromechanical transducer transfers the mechanical oscillations or waves with a frequency of 60 KHz.

* * * * *